United States Patent [19]

Klingler et al.

[11] Patent Number: 5,703,050

[45] Date of Patent: Dec. 30, 1997

[54] UREA DERIVATIVES, THEIR PREPARATION AND USE

[75] Inventors: Otmar Klingler, Rodgau; Gerhard Zoller, Schöneck; Bernd Jablonka, Bad Soden; Melitta Just, Langen; Gerhard Breipohl, Frankfurt am Main; Jochen Knolle, Kriftel; Wolfgang König, Stallwang; Hans Ulrich Stilz, Frankfurt am Main, all of Germany

[73] Assignee: Hoechst Aktiengesellschaft, Frankfurt am Main, Germany

[21] Appl. No.: 513,815

[22] PCT Filed: Mar. 9, 1994

[86] PCT No.: PCT/EP94/00713

§ 371 Date: Jan. 17, 1996

§ 102(e) Date: Jan. 17, 1996

[87] PCT Pub. No.: WO94/22907

PCT Pub. Date: Oct. 13, 1994

[30] Foreign Application Priority Data

Mar. 26, 1993 [DE] Germany .................. 43 09 867.3

[51] Int. Cl.$^6$ .................. A61K 38/00; C07K 5/00
[52] U.S. Cl. .................. 514/18; 530/330; 530/331
[58] Field of Search .................. 530/330, 331; 514/18

[56] References Cited

U.S. PATENT DOCUMENTS

| | | | |
|---|---|---|---|
| 5,051,405 | 9/1991 | Klein et al. | 514/18 |
| 5,053,392 | 10/1991 | Klein et al. | 514/18 |
| 5,272,162 | 12/1993 | Tjoeng et al. | 514/344 |
| 5,314,902 | 5/1994 | Tjoeng et al. | 514/357 |
| 5,389,614 | 2/1995 | Konig et al. | 514/18 |

FOREIGN PATENT DOCUMENTS

| | | |
|---|---|---|
| B-73653 | 10/1991 | Australia . |
| 449079 | 10/1991 | European Pat. Off. . |
| 512829 | 11/1992 | European Pat. Off. . |
| 513675 | 11/1992 | European Pat. Off. . |
| 4126277 | 2/1993 | Germany . |
| WO92/13552 | 8/1992 | WIPO . |

OTHER PUBLICATIONS

Effect of RGD Peptide on Cell Adhesion, by Kumagai et al., Biomedical and Biophysical Research Comm., vol. 177, No. 1 (1991), pp. 74–82.

A novel Arg–Gly–Asp Containing Peptide, etc, by Isoai et al., Cancer Letters, vol. 65, pp.255 to 263, (1992), Elsevier Pub. Ireland.

Modulation of Vitronectin Receptor–Mediated Osteoclast Adhesion, etc., Horton et al., Journal of Bone & Mineral Research, vol. 8, No. 2, pp. 239–247 (1993).

Synthetic Peptide Containing Arg–Gly–Asp Inhibits Bone Formation, etc., by Gronowicz et al., Journal of Bone & Mineral Research, vol. 9, No. 2, pp. 193 to 201 (1994).

*Primary Examiner*—Cecilia J. Tsang
*Assistant Examiner*—Bennett Celsa
*Attorney, Agent, or Firm*—Perman & Green, LLP

[57] ABSTRACT

Urea derivates are disclosed having the formula (I).

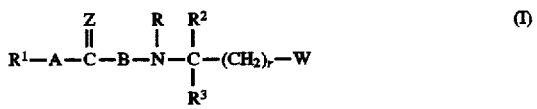

in which A, B, W, Z, R, $R^1$, $R^2$, $R^3$ and r have the meaning given in the description, as well as a process for preparing the same and their use as inhibitors of thrombocyte aggregation, carcinom cell metastasis and osteoclast binding to bone surface.

9 Claims, No Drawings

UREA DERIVATIVES, THEIR PREPARATION AND USE

This application is a 37, of PCT/EP 94/00713 filed Mar. 9, 1994.

FIELD OF THE INVENTION

The present invention relates to substituted ureas and thioureas, their preparation and their use as medicines, in particular as inhibitors of blood platelet aggregation.

DESCRIPTION OF THE RELATED ART

EP-A 449 079 and EP-A 530 505 describe hydantoin derivatives which have platelet aggregation-inhibiting effects. Structurally related urea derivatives are mentioned in WO-A 92 13552 and EP-A 512 829. Further investigations showed that the urea derivatives of the present invention are also potent inhibitors of blood platelet aggregation.

SUMMARY OF THE INVENTION

The present invention relates to urea derivatives of the general formula I $$R^1-A-\overset{Z}{\overset{\|}{C}}-B-N-\overset{R}{\overset{|}{C}}-\overset{R^2}{\underset{R^3}{|}}-(CH_2)_r-W,$$

in which r denotes an integer from 0 to 3;

Z denotes oxygen or sulphur;

W denotes —COW$^1$, tetrazolyl, —SO$_2$—OH or —SO$_2$NHR$^9$;

W$^1$ denotes hydroxyl, (C$_1$–C$_{28}$)-alkoxy, (C$_6$–C$_{14}$)-aryl-(C$_1$–C$_8$)-alkoxy, which can also be substituted in the aryl radical, optionally substituted (C$_6$–C$_{14}$)-aryloxy, amino or mono- or di-((C$_1$–C$_{18}$)-alkyl)amino;

A denotes —(CH$_2$)$_k$—NR$^a$—, in which k stands for an integer from 1 to 4, or

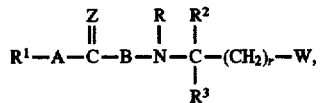

in which n and p independently of one another stand for an integer from 0 to 4;

B denotes —NR$^b$—(CH$_2$)$_m$—CO—, in which m stands for an integer from 1 to 4, or —NR$^b$—CHR$^c$—CO—, in which R$^c$ denotes an amino acid side chain, or

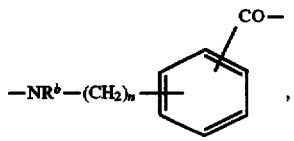

in which n stands for an integer from 0 to 4, or

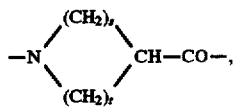

in which s and t independently of one another can stand for an integer from 0 to 5, but the sum of s and t must be a number between 2 and 5. but where, if R stands for hydrogen, r denotes the number 1 and A stands for —(CH$_2$)$_k$—NR$^a$—, in which k stands for an integer from 2 to 4, or for

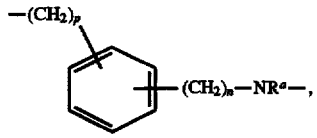

in which p is other than 0, then B cannot simultaneously stand for —NR$^b$—(CH$_2$)$_m$—CO—, in which m stands for the numbers 1 or 2;

R$^a$ and R$^b$ independently of one another denote hydrogen, hydroxyl. (C$_1$–C$_{18}$)-alkyl. (C$_6$–C$_{14}$)-aryl, (C$_6$–C$_{14}$)-aryl-(C$_1$–C$_8$)-alkyl, hydroxycarbonyl-(C$_1$–C$_6$)-alkyl, (C$_1$–C$_6$)-alkoxycarbonyl-(C$_1$–C$_6$)-alkyl, (C$_6$–C$_{14}$)-aryloxycarbonyl-(C$_1$–C$_6$)-alkyl, (C$_6$–C$_{14}$)-aryl-(C$_1$–C$_6$)-alkoxycarbonyl-(C$_1$–C$_6$)-alkyl, (C$_1$–C$_{28}$)-alkoxy, (C$_6$–C$_{14}$)-aryloxy, (C$_6$–C$_{14}$)-aryl-(C$_1$–C$_8$)-alkoxy, (C$_1$–C$_6$)-alkylcarbonyloxy, (C$_1$–C$_6$)-alkoxycarbonyloxy, (C$_6$–C$_{14}$)-aryloxycarbonyloxy or (C$_6$–C$_{14}$)-aryl-(C$_1$–C$_6$)-alkoxycarbonyloxy, where the aryl radicals can also be substituted;

R denotes hydrogen or (C$_1$–C$_6$)-alkyl;

R$^1$ denotes —NH—X or —C(=NX)—NH$_2$;

X denotes hydrogen, (C$_1$–C$_6$)-alkyl, (C$_1$–C$_6$)-alkylcarbonyl, (C$_1$–C$_6$)-alkoxycarbonyl, (C$_1$–C$_{18}$)-alkylcarbonyloxy-(C$_1$–C$_6$)-alkoxycarbonyl, optionally substituted (C$_6$–C$_{14}$)-arylcarbonyl, optionally substituted (C$_6$–C$_{14}$)-aryloxycarbonyl, (C$_6$–C$_{14}$)-aryl-(C$_1$–C$_6$)-alkoxycarbonyl, which can also be substituted in the aryl radical, cyano, hydroxyl, (C$_1$–C$_6$)-alkoxy or amino or a radical of the formula II where R' and R" independently of one another stand for hydrogen, (C$_1$–C$_6$)-alkyl, trifluoro-(C$_1$–C$_6$)-alkyl, (C$_1$–C$_6$)-alkoxycarbonyl, (C$_1$–C$_6$)-alkylcarbonyl, optionally substituted (C$_6$–C$_{14}$)-arylcarbonyl, (C$_1$–C$_{18}$)-alkylcarbonyloxy-(C$_1$–C$_6$)-alkoxycarbonyl, optionally substituted (C$_6$–C$_{14}$)-aryloxycarbonyl, (C$_6$–C$_{14}$)-aryl-(C$_1$–C$_6$)-alkoxycarbonyl, which can also be substituted in the aryl radical, cyano, hydroxyl, (C$_1$–C$_6$)-alkoxy or amino;

R$^2$ denotes hydrogen, (C$_1$–C$_4$)-alkyl, (C$_2$–C$_6$)-alkynyl, phenyl or a mono- or bicyclic up to 8-membered heterocyclic ring, which can be aromatic, partially hydrogenated or completely hydrogenated and which can contain one, two or three identical or different heteroatoms from the series nitrogen, oxygen and sulphur, where the (C$_1$–C$_4$)-alkyl and the phenyl can be unsubstituted or mono- or polysubstituted by identical or different radicals from the series hydroxyl, amino, (C$_1$–C$_4$)-alkoxy, imidazolyl, indolyl, pyrrolidinyl, hydroxypyrrolidinyl, phenyl or halogen and the heterocyclic ring can be unsubstituted or mono- or poly-substituted by identical or different radicals from the series (C$_1$–C$_{18}$)-alkyl, phenyl, phenyl-(C$_1$–C$_4$)-alkyl, (C$_1$–C$_{18}$)-alkoxy, phenyl-(C$_1$–C$_4$)-alkoxy, halogen, nitro, amino, hydroxyl, trifluoromethyl or oxo or, in the case of nitrogen heterocycles, can be present as N-oxide;

$R^3$ denotes hydrogen, —COOR$^4$, —CO—N(CH$_3$)R$^4$ or —CO—NH—R$^4$;

$R^4$ denotes hydrogen or (C$_1$–C$_{28}$)-alkyl, which can optionally be mono- or polysubstituted by identical or different radicals from the series hydroxyl, hydroxycarbonyl, aminocarbonyl, mono- or di-((C$_1$–C$_{18}$)-alkyl)aminocarbonyl, amino-(C$_2$–C$_{18}$)-alkylaminocarbonyl, amino-(C$_1$–C$_3$)-alkylphenyl-(C$_1$–C$_3$)-alkylaminocarbonyl, (C$_1$–C$_{18}$)-alkylcarbonylamino-(C$_1$–C$_3$)-alkylphenyl-(C$_1$–C$_3$)-alkylaminocarbonyl, (C$_1$–C$_{18}$)-alkylcarbonylamino-(C$_2$–C$_{18}$)-alkylaminocarbonyl, (C$_6$–C$_{14}$)-aryl-(C$_1$–C$_8$)-alkoxycarbonyl, which can also be substituted in the aryl radical, amino, mercapto, (C$_1$–C$_{18}$)-alkoxy, (C$_1$–C$_{18}$)-alkoxycarbonyl, optionally substituted (C$_3$–C$_8$)-cycloalkyl, halogen, nitro, trifluoromethyl or by the radical R$^5$, where $R^5$ denotes optionally substituted (C$_6$–C$_{14}$)-aryl, (C$_6$–C$_{14}$)-aryl-(C$_1$–C$_8$)-alkyl, optionally substituted in the aryl radical, a mono- or bicyclic 5- to 12-membered heterocyclic ring, which can be aromatic, partially hydrogenated or completely hydrogenated and which can contain one, two or three identical or different heteroatoms from the series nitrogen, oxygen and sulphur, a radical R$^6$ or a radical R$^6$CO—, where the aryl and, independently thereof, the heterocyclic radical can be mono- or polysubstituted by identical or different radicals from the series (C$_1$–C$_{18}$)-alkyl, (C$_1$–C$_{18}$)-alkoxy, phenyl-(C$_1$–C$_4$)-alkoxy, phenyl, phenyl-(C$_1$–C$_4$)-alkyl, halogen, nitro, amino, hydroxyl or trifluromethyl and the heterocyclic radical can also be mono- or polysubstituted by oxo or, in the case of nitrogen heterocycles, can be present as N-oxide;

$R^6$ denotes —NR$^7$R$^8$, —OR$^7$, —SR$^7$, —SO$_2$—OH, —SO$_2$—NHR$^9$, tetrazolyl, an amino acid side chain, a natural or unnatural amino acid, imino acid, optionally N-(C$_1$–C$_8$)-alkylated or N-((C$_6$–C$_{14}$)-aryl-(C$_1$–C$_8$)-alkylated) azaamino acid radical or a dipeptide radical, which can also be substituted in the aryl radical and/or in which the peptide bond can be reduced to —NH—CH$_2$—, and also their esters and amides, where free functional groups can optionally be replaced by hydrogen or hydroxymethyl or protected by protective groups customary in peptide chemistry;

$R^7$ denotes hydrogen, (C$_1$–C$_{18}$)-alkyl, (C$_6$–C$_{14}$)-aryl-(C$_1$–C$_8$)-alkyl, (C$_1$–C$_{18}$)-alkylcarbonyl, (C$_1$–C$_{18}$)alkoxycarbonyl, (C$_6$–C$_{14}$)-arylcarbonyl, (C$_6$–C$_{14}$)-aryl-(C$_1$–C$_8$)-alkylcarbonyl or (C$_6$–C$_{14}$)-aryl-(C$_1$–C$_{18}$)-alkoxycarbonyl, where the alkyl groups can optionally be substituted by an amino group and/or where the aryl radicals can be mono- or polysubstituted, preferably monosubstituted, by identical or different radicals from the series (C$_1$–C$_8$)-alkyl, (C$_1$–C$_8$)-alkoxy, halogen, nitro, amino and trifluoromethyl, a natural or unnatural amino acid, imino acid, optionally N-(C$_1$–C$_8$)-alkylated or N-((C$_6$–C$_{14}$)-aryl-(C$_1$–C$_8$)-alkylated) azaamino acid radical or a dipeptide radical, which can also be substituted in the aryl radical and/or in which the peptide bond can be reduced to —NH—CH$_2$—;

$R^8$ denotes hydrogen, (C$_1$–C$_{18}$)-alkyl, optionally substituted (C$_6$–C$_{14}$)-aryl or (C$_6$–C$_{14}$)-aryl-(C$_1$–C$_8$)-alkyl, which can also be substituted in the aryl radical;

$R^9$ denotes hydrogen, aminocarbonyl, (C$_1$–C$_{18}$)-alkylaminocarbonyl, (C$_3$–C$_8$)-cycloalkylaminocarbonyl, (C$_1$–C$_{18}$)-alkyl or (C$_3$–C$_8$)-cycloalkyl.

and their physiologically tolerable salts.

Cycloalkyl radicals are in particular cyclopropyl, cyclobutyl, cyclopentyl, cyclohexyl, cycloheptyl and cyclooctyl, which, however, can also be substituted, by, for example, (C$_1$–C$_4$)-alkyl. Examples of substituted cycloalkyl radicals are 4-methylcyclohexyl and 2,3-dimethylcyclopentyl.

Alkyl radicals can be straight-chain or branched. This also applies if they carry substituents or occur as substituents of other radicals. Examples of suitable (C$_1$–C$_{28}$)-alkyl radicals are: methyl, ethyl, propyl, butyl, pentyl, hexyl, heptyl, octyl, decyl, undecyl, dodecyl, tridecyl, pentadecyl, hexadecyl, heptadecyl, octadecyl, nonadecyl, eicosyl, docosyl, tricosyl, pentacosyl, hexacosyl, heptacosyl, octacosyl, isopropyl, isobutyl, isopentyl, neopentyl, isohexyl, 3-methylpentyl, 2,3,5-trimethylhexyl, sec-butyl, tert-butyl, tert-pentyl. Preferred alkyl radicals are methyl, ethyl, propyl, isopropyl, butyl, isobutyl, sec-butyl and tert-butyl.

(C$_2$–C$_6$)-alkynyl radicals can be straight-chain or branched. Examples are ethynyl, 1-propynyl, 2-propynyl, 2-butynyl, 1-hexenyl, 5-hexenyl or 3,3-dimethyl-1-butynyl.

(C$_6$–C$_{14}$)-aryl groups are, for example, phenyl, naphthyl, biphenylyl or fluorenyl, phenyl and naphthyl being preferred. The same applies to radicals such as aralkyl or arylcarbonyl. Aralkyl radicals are in particular benzyl and also 1- and 2-naphthylmethyl, which can also be substituted. Substituted aralkyl radicals are, for example, halobenzyl or (C$_1$–C$_4$)-alkoxybenzyl.

If phenyl is disubstituted, the substituents can be in the 1,2-, 1,3- or 1,4-position relative to one another. The 1,3- and the 1,4-positions are preferred.

Mono- or bicyclic 5- to 12-membered heterocyclic rings and 5- to 8-membered heterocyclic rings are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or a benza-fused or cyclopenta-, cyclohexa- or cyclo-hepta-fused derivative of these radicals.

These heterocycles can be aromatic or partially or completely saturated and unsubstituted or monosubstituted by identical or different radicals from the series (C$_1$–C$_{18}$)-alkyl, phenyl, phenyl-(C$_1$–C$_4$)-alkyl, (C$_1$–C$_{18}$)-alkoxy, phenyl-(C$_1$–C$_4$)-alkoxy, halogen, nitro, amino, hydroxyl, trifluoromethyl or oxo. There can be substituents on one or more nitrogen atoms and/or on one or more carbon atoms. Preferred substituents on nitrogen atoms are (C$_1$–C$_7$)-alkyl, e.g. methyl or ethyl, phenyl or phenyl-(C$_1$–C$_4$)-alkyl, e.g. benzyl, on carbon atoms (C$_1$–C$_4$)-alkyl, halogen, hydroxyl, (C$_1$–C$_4$)-alkoxy, e.g. methoxy, phenyl-(C$_1$–C$_4$)-alkoxy, e.g. benzyloxy, or oxo. Nitrogen heterocycles can also be present as N-oxides.

Radicals of this type, are, for example, 2- or 3-pyrrolyl, phenylpyrrolyl, e.g. 4- or 5-phenyl-2-pyrrolyl, 2-furyl, 2-thienyl, 4-imidazolyl, methylimidazolyl, e.g. 1-methyl-2-, 4- or 5-imidazolyl, 1,3-oxazol-2-yl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g. 1-methyl-, 5-methyl-, 5-methoxy-, 5-benzyloxy-, 5-chloro- or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4- quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl. Partially hydrogenated or completely hydrogenated heterocyclic rings are, for example, dihydropyridinyl, pyrrolidinyl, e.g. 2-, 3- or 4-(N-methylpyrrolidinyl), piperazinyl, morpholinyl, thiomorpholinyl, tetrahydrothienyl or benzodioxolanyl.

Halogen stands for fluorine, chlorine, bromine or iodine, in particular for fluorine or chlorine.

Natural and unnatural amino acids can be present, if chiral, in the D- or L-form. α-Amino acids are preferred. Examples which may be mentioned (cf. Houben-Weyl, Methoden der organischen Chemie [Methods of Organic Chemistry], Volume XV/1 and 2, Stuttgart, 1974) are:

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, , βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid, 2-(p-chlorophenyl)aminoacetic acid.

Amino acid side chains are understood as meaning side chains of natural or unnatural amino acids. Azaamino acids are natural or unnatural amino acids in which the central component

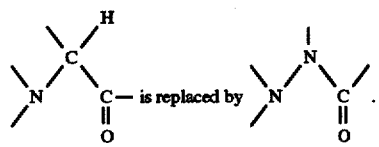

Suitable radicals of an imino acid are in particular radicals of heterocycles from the following group: pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]-pyrrole-2-carboxylic acid; 2-azabicyclo [2.2.2]octane-3-carboxylic acid; 2 -azabicyclo [2.2.1]heptane-3 -carboxylic acid; 2 -azabicyclo-[3.1.0] hexane-3-carboxylic acid; 2-azaspiro [4.4]nonane-3-carboxylic acid; 2 -azaspiro [4.5]decane-3 -carboxylic acid; spiro-(bicyclo[2.2.1]heptane)-2,3-pyrrolidine-5-carboxylic acid; spiro (bicyclo [2.2.2]octane)-2,3 -pyrrolidine-5-carboxylic acid; 2-azatricyclo[4.3.0.1.$^{6.9}$]decane-3-carboxylic acid; decahydrocyclohepta[b]pyrrole-2-carboxylic acid; decahydrocycloocta [c]pyrrole-2-carboxylic acid; octahydrocyclopenta[c]pyrrole-2-carboxylic acid; octahydroisoindole-1-carboxylic acid; 2,3, 3a, 4,6a-hexa-hydrocyclopenta[b]pyrrole-2-carboxylic acid; 2,3,3a,4,5,7a-hexahydroindole-2- carboxylic acid; tetrahydrothiazole-4-carboxylic acid; isoxazolidine-3-carboxylic acid; pyrazolidine-3-carboxylic acid; hydroxypyrrolidine-2-carboxylic acid; which all can be optionally substituted (see following formulae):

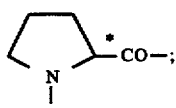

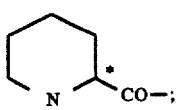

-continued

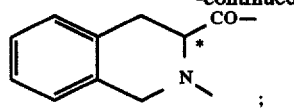

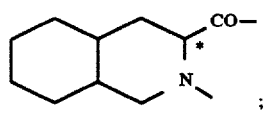

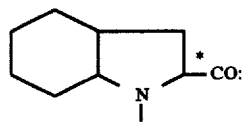

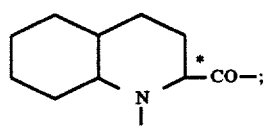

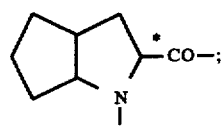

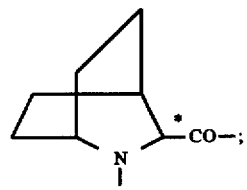

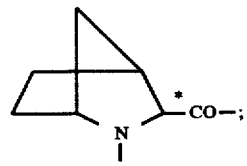

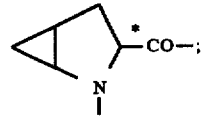

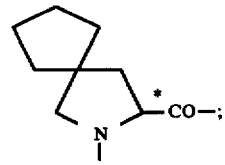

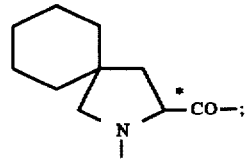

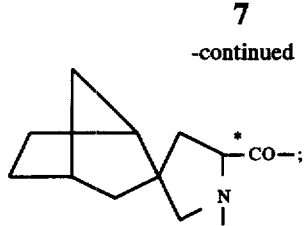
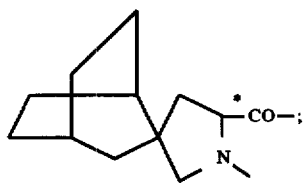
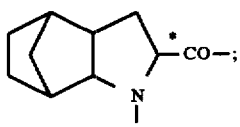
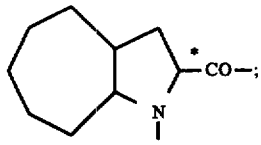
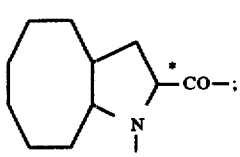
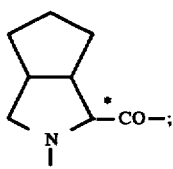
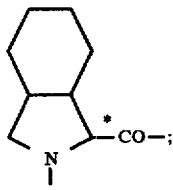
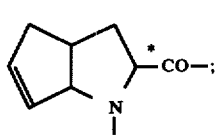
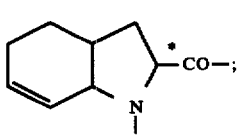

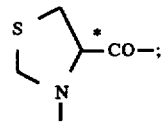
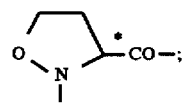
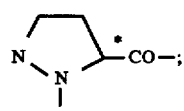
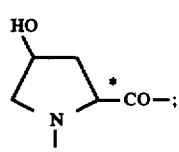

The heterocycles on which the abovementioned radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A271,865 and EP-A 344,682.

Dipeptides can contain natural or unnatural amino acids, amino acids and also azaamino acids as components. Furthermore, the natural or unnatural amino acids, amino acids, azaamino acids and dipeptides can also be present as esters or amides, such as e.g. metal ester, ethyl ester, isopropyl ester, isobutyl ester, tert-butyl ester, benzyl ester, ethylamide, semicarbazide or ω-amino-$(C_2–C_8)$-alkylamide.

Functional groups of the amino acids, imino acids and dipeptides can be present in protected form. Suitable protective groups such as e.g. urethane protective groups, carboxyl protective groups and side chain protective groups are described in Hubbuch, Kontakte (Merck) 1979, No. 3, pages 14 to 23 and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

Physiologically tolerable salts of the compounds of the general formula I are in particular pharmaceutically utilizable or non-toxic salts.

Such salts are formed, for example, from compounds of the general formula I which contain acidic groups, e.g. carboxyl, with alkali metals or alkaline earth metals, such as e.g. Na, K, Mg and Ca, and also with physiologically tolerable organic amines, such as e.g. triethylamine, ethanolamine or tris(2-hydroxyethyl)amine.

Compounds of the general formula I which contain basic groups, e.g. an amino group, an amidino group or a guanidino group, for salts with inorganic acids, such as e.g. hydrochloric acid, sulphuric acid or phosphoric acid and with organic carboxylic or sulphonic acid, such as e.g. acetic acid, citric acid, benzoic acid, maleic acid, fumaric acid, tartaric acid, methanesulphonic acid or p-toluenesulphonic acid.

The compounds of the general formula I according to the invention can contain optically active carbon atoms and can thus be present in the form of pure enantiomers or in the form of enantiomer mixtures. Both pure enantiomers and enantiomer mixtures and diastereomers and diastereomer mixtures are subjects of the present invention.

The compounds of the general formula I according to the invention can moreover contain mobile hydrogen atoms, i.e. can be present in various tautomeric forms. These tautomers are also a subject of the present invention.

DESCRIPTION OF THE PREFERRED EMBODIMENTS

Preferred compounds of the general formula I are those in which r denotes the number 1;

W denotes —$COW^1$;

$W^1$ denotes hydroxyl, ($C_1$–$C_4$)-alkoxy, in particular methoxy, ethoxy, 2-propyloxy, isobutyloxy or tert-butyloxy, or benzyloxy;

A denotes —$(CH_2)_k$—$NR^a$—, in which k stands for the numbers 1 or 2, or

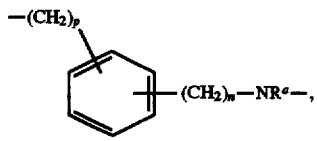

in which n stands for the numbers 0 or 1 and p stands for the number 0;

B denotes —$NR^b$—$(CH_2)_m$—CO—, in which m stands for the numbers 1 or 2, or —$NR^b$—$CHR^c$—CO—, in which $R^c$ stands for the side chain of the amino acids alanine, valine, phenylalanine, tyrosine, leucine, isoleucine, tryptophan, lysine, histidine, asparagine, glutamine or phenylglycine, or

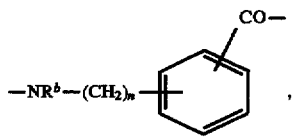

in which n stands for the numbers 0 or 1, or

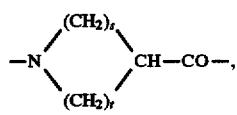

in which s and t independently of one another can stand for an integer from 0 to 4, the sum of s and t, however, must give the number 3 or the number 4, where, however, if A stands for —$(CH_2)_k$—$NR^a$— and k therein stands for 2, then B cannot simultaneously denote —$NR^b$—$(CH_2)_m$—CO—;

R denotes hydrogen;

X denotes hydrogen, ($C_1$–$C_6$)-alkoxycarbonyl, ($C_1$–$C_6$)-alkylcarbonyl, ($C_1$–$C_{18}$)-alkylcarbonyloxy-($C_1$–$C_8$)-alkoxycarbonyl, ($C_6$–$C_{14}$)-aryl-($C_1$–$C_6$)-alkoxycarbonyl or a radical of the formula

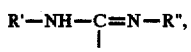

in which R' and R" independently of one another stand for hydrogen, trifluoroethyl, ($C_1$–$C_6$)-alkylcarbonyl, ($C_1$–$C_6$)-alkoxycarbonyl, ($C_1$–$C_{18}$)-alkylcarbonyloxy-($C_1$–$C_6$)-alkoxycarbonyl or ($C_6$–$C_{14}$)-aryl-($C_1$–$C_6$)-alkoxycarbonyl;

$R^2$ denotes hydrogen;

$R^3$ denotes —CO—NH—$R^4$, where —NH—$R^4$ stands for the radical of an α-amino acid, its ω-amino-($C_2$–$C_8$)-alkylamide or its ($C_1$–$C_8$)-alkyl or benzyl ester, or where $R^4$ denotes methyl which is substituted by an amino acid side chain and by a radical from the series —$SO_2$—OH, —$SO_2$—$NHR^9$ and tetrazolyl.

Radicals of α-amino acids standing for —NH—$R^4$ are in this case particularly preferably the valine, lysine, phenylalanine, phenylglycine or 4-chlorophenylglycine radical. If —NH—$R^4$ in this case stands for an ester of one of these α-amino acids, the methyl, ethyl, isopropyl, isobutyl, tert-butyl ester or benzyl ester is preferred.

Compounds of the formula I can be prepared by fragment condensation of a compound of the general formula III

with a compound of the general formula IV

where the radicals A, B, W, Z, R, $R^1$, $R^2$ and $R^3$ and also r are defined as indicated above.

The starting compounds of the general formula IV are as a rule synthesized stepwise from the C-terminal end. For condensation of the compounds of the general formula III with those of the general formula IV, the coupling methods of peptide chemistry known per se (see e.g. Houben-Weyl, Methoden der Organischen Chris [Methods of Organic Chemistry], Volumes 15/1 and 15/2, Stuttgart, 1974) are advantageously used. For this coupling, it is as a rule necessary that amino groups contained in $R^1$, $R^2$, $R^3$ and W are protected by reversible protective groups during the condensation. The same applies to the carboxyl groups of the compounds of the formula IV, which are preferably present as ($C_1$–$C_6$)-alkyl, benzyl or tert-butyl esters. Amino group protection is unnecessary if the amino groups to be generated are still present as nitro or cyano groups and are only formed, after coupling, by hydrogenation. After coupling, the protective groups present are removed in a suitable manner. For example, $NO_2$ groups (guanidino protection), benzyloxycarbonyl groups and benzyl esters can be removed by hydrogenation. The protective groups of the tert-butyl type are cleaved by acid, while the 9-fluorenyl-methoxycarbonyl radical is removed by means of secondary amines.

The starting compounds of the general formula III can be obtained as follows:

Amine derivatives of the general formula V or amine derivatives of the general formula VI in which, as shown by way of example, the carboxylic acid group can be present as the methyl ester, where A, B and $R^1$

have the meanings indicated above, can be reacted with reactive carbonic acid derivatives of the general formula VII in which Z stands for oxygen or sulphur and the two radicals Q are identical or different leaving groups, to give the compounds of the general formula VIII or the compounds of the general formula IX $$R^1-A-\overset{\overset{Z}{\|}}{C}-Q \quad \text{(VIII)}$$

$$Q-\overset{\overset{Z}{\|}}{C}-B-OCH_3 \quad \text{(IX)}$$

Suitable leaving groups Q are, for example, halides, in particular chloride, ($C_1$–$C_4$)-alkoxy, for example methoxy, ethoxy, or isobutoxy, ($C_1$–$C_4$)-alkylthio, for example methylthio or ethylthio, unsubstituted ($C_6$–$C_{14}$)-aryloxy, in particular phenoxy, mono- or polysubstituted ($C_6$–$C_{14}$)-aryloxy, particular subsituted phenoxy, for example 4-nitrophenoxy, 4-chlorophenoxy or 2,4,5-trichlorophenoxy, or di- and triazolyl radicals, for example imidazolyl or triazolyl. Examples of reactive carbonic acid derivatives are thus phosgene, which can also be employed in the form of di- or triphosgene, thiophosgene, alkyl and aryl chloroformates, dialkyl and diaryl carbonates, in which the two radicals can also be different, thiocarbonates, N, N'-carbonyldiimidazole, N,N'-thiocarbonyldiimidazole, 1,1'-carbonyldi-1,2,4-triazole or 1,1'-carbonyldibenzotriazole. The condensation of the compounds of the general formula VIII with the compounds of the general formula VI or the condensation of the compounds of the general formula IX with the compounds of the general formula V yields, after alkaline hydrolysis, the compounds of the general formula III (see e.g. Houben-Weyl, Methoden der Organischen Chemie [Methods of Organic Chemistry], Volumes VIII and E4, Stuttgart 1952 and 1983 respectively).

If one of the two radicals $R^a$ and $R^b$ stands for hydrogen or both stand for hydrogen, the starting compounds of the general formula III can also be prepared using heterocumulenes:

The reaction of aminocarboxylic acid esters, for example of the general formula VI $$H-B-OCH_3 \quad \text{(VI)}$$

in which B has the meanings indicated above, with an isocyanate or an isothiocyanate of the general formula X $$R^1-Y^a-N=C=Z \quad \text{(X)}$$

in which $R^1$ and Z have the meanings indicated above and $Y^a$ stands for —$(CH_2)_k$— or —$(CH_2)_p$—⬡—$(CH_2)_n$—, in which k, n and p have the meanings indicated above, leads to the compounds of the general formula IIIa $$R^1-Y^a-N-\overset{\overset{Z}{\|}}{C}-B-OCH_3 \quad \text{(IIIa)}$$
$$\phantom{R^1-Y^a-N}H$$

or—after alkaline hydrolysis of the ester group—to the corresponding carboxylic acids.

The reaction of amine derivatives of the general formula V $$R^1-A-H \quad \text{(V)}$$

in which $R^1$ and A have the meanings indicated above, with an isocyanato- or isothiocyanatocarboxylic acid ester of the general formula XI $$Z=C=N-Y^b-OCH_3 \quad \text{(XI)}$$

in which Z stands for oxygen or sulphur and $Y^b$ stands for —$(CH_2)_m$—CO— or —$CHR^r$—CO— or —$(CH_2)_n$—⬡—CO—, in which $R^r$ and m and n have the meanings indicated above, leads to the compounds of the general formula IIIb $$R^1-A-\overset{\overset{Z}{\|}}{C}-N-Y^b-OCH_3 \quad \text{(IIIb)}$$
$$\phantom{R^1-A-C-N}H$$

or—after alkaline hydrolysis of the ester group—to the corresponding carboxylic acids.

In all reaction steps, functional groups which may be free must be protected by suitable reversible protective groups, which are later removed again in a suitable manner.

For the guanylation and nitroguanylation of the amino compounds the following reagents can be used:

1. O-Methylisourea
    (S. Weiss and H. Krommer, Chemiker Zeitung 98 (1974) 617–618),
2. S-Methylisothiourea
    R. F. Borne, M. L. Forrester and I. W. Waters, J. Med. Chem. 20 (1977) 771–776),
3. Nitro-S-Methylisothiourea
    (L. S. Hafner and R. E. Evans, J. Org. Chem. 24 (1959) 1157),
4. Formamidinesulphonic acid
    (K. Kim, Y. T. Lin and H. S. Mosher, Tetrahedron Lett. 29 (1988) 3183–3186),
5. 3,4-Dimethyl-1-pyrazolylformamidinium nitrate
    (F. L. Scott, D. G. O'Donovan and J. Reilly, J, Amer. Chem. Soc. 75 (1953) 4053–4054),
6. N,N'-Di-tert-butyloxycarbonyl-S-methylisothiourea
    (R. J. Bergeron and J. S. McManis, J. Org. Chem. 52 (1987) 1700–1703),
7. N-Alkoxycarbonyl-, N,N'-dialkoxycarbonyl-, N-alkylcarbonyl- and N,N'-dialkylcarbonyl-S-methylisothiourea
    (H. Wollweber, H. Kölling, E. Niemers, A. Widding, P. Andrews, H. P. Schulz and H. Thomas, Arzneim. Forsch./ Drug Res. 34 (1984) 531–542).

Amidines can be prepared from the corresponding cyano compounds by addition of alcohols (e.g. methanol or ethanol) in acidic anhydrous medium (e.g. dioxane, methanol or ethanol) and subsequent aminolysis (G. Wagner, P. Richter and Ch. Garbs, Pharmazie 29 (1974) 12–15). A further method of preparing amidines is the addition of $H_2S$ to the cyano group, followed by a methylation of the resulting thioamide and subsequent reaction with ammonia (GDR patent no. 235 866).

The compounds of the general formula I and their physiologically tolerable salts can be administered as medicines per se, in mixtures with one another or in the form of pharmaceutical preparations which permit enteral or parenteral administration and which contain as active constituent an effective dose of at least one compound of the general formula I or of an acid addition salt thereof, in addition to customary pharmaceutically innocuous excipients and additives. The preparations normally contain about 0.5 to 90% by weight of the therapeutically active compound.

The medicines can be administered orally, e.g. in the form of pills, tablets, lacquered tablets, sugar-coated tablets, granules, hard and soft gelatine capsules, solutions, syrups, emulsions or suspensions or aerosol mixtures. However, administration can also be carried out rectally, e.g. in the form of suppositories, or parenterally, e.g. in the form of injection or infusion solutions or microcapsules, percutaneously, e.g. in the form of ointments or tinctures, or nasally, e.g. in the form of nasal sprays.

The pharmaceutical preparations are prepared in a manner known per se, pharmaceutically inert inorganic or organic excipients being used. For the preparation of pills, tablets, sugar-coated tablets and hard gelatine capsules, use can be made of e.g. lactose, maize starch or derivatives thereof, talc, stearic acid or its salts, etc. Excipients for soft gelatine capsules and suppositories are e.g. fats, waxes, semi-solid and liquid polyols, natural or hardened oils etc. Suitable excipients for the preparation of solutions and syrups are e.g. water, sucrose, invert sugar, glucose, polyols etc. Suitable excipients for the preparation of injection solutions are water, alcohols, glycerol, polyols, vegetable oils etc. Suitable excipients for microcapsules or implants are copolymers of glycolic acid and lactic acid.

Besides the active compounds and excipients, the pharmaceutical preparations can also contain additives, such as e.g. fillers, extenders, disintegrants, binders, lubricants, wetting agents, stabilizers, emulsifiers, preservatives, sweeteners, colourants, flavourings or aromatizers, thickeners, diluents, buffering substances, and further solvents or solubilizers or agents for achieving a depot effect, and also salts for changing the osmotic pressure, coating compositions or antioxidants. They can also contain two or more compounds of the general formula I or their pharmacologically acceptable acid addition salts and additionally one or more other therapeutically active substances.

Other therapeutically active substances of this type are, for example, circulation-promoting agents, such as dihydroergocristine, nicergoline, buphenine, nicotinic acid and its esters, pyridylcarbinol, bencyclan, cinnarizine, naftidrofuryl, raubasine and vincamine; positively inotropic compounds, such as digoxin, acetyldigoxin, metildigoxin and lanatoglycosides; coronary dilators, such as carbochromen; dipyridamol, nifedipine and perhexiline; antianginal compounds, such as isosorbide dinitrate, isosorbide mononitrate, glycerol nitrate, molsidomin and verapamil; β-blockers, such as propranolol, oxprenolol, atenolol, metoprolol and penbutolol. Moreover, the compounds can also be combined, for example, with nootropically active substances, such as e.g. piracetam, or CNS-active substances, such as pirlindol, sulpiride etc.

The dose can vary within wide limits and is to be suited to the individual conditions in each individual case. In general, in the case of oral administration a daily dose of about 0.1 to 1 mg/kg, preferably 0.3 to 0.5 mg/kg, of body weight is appropriate to achieve effective results, in the case of intravenous administration, the daily dose is in .general about 0.01 to 0.3 mg/kg, preferably 0.05 to 0.1 mg/kg, of body weight.

The daily dose can be divided, in particular in the case of the administration of relatively large amounts, into several, e.g. 2, 3 or 4, part administrations. If appropriate, depending on individual behaviour, it may be necessary to deviate upwards or downwards from the daily dose indicated. Pharmaceutical preparations normally contain 0.2 to 50 mg, preferably 0.5 to 10 mg, of active compound of the general formula I or of one of its pharmaceutically acceptable salts per dose.

The urea derivatives of the formula I according to the invention have the ability to inhibit the binding of fibrinogen, fibronectin and of the von Willebrand factor to integrin receptors. In this manner, they affect the cell-cell and cell-matrix interaction and can thus prevent the formation of blood platelet thrombi. Integrins are cell membrane glycoproteins and mediate cell adhesion by interaction with a plurality of extracellular proteins such as fibronectin, laminin, collagen, vitronectin, and von Willsbrand factor or with other cell membrane proteins such as e.g. ICAM-1. An important receptor from the integrin family is the glycoprotein IIb/IIIa localized on blood platelets (fibrinogen receptor)- a key protein of platelet-platelet interaction and thrombus formation. A central fragment in the receptor recognition sequence of these proteins is the tripeptide Arg-Gly-Asp (E. Ruoslahti and M. D. Pierschbacher, Science 238 (1987) 491–497; D. R. Phillips, I. F. Charo, L. V. Parise and L. A. Fitzgerald, Blood 71 (1988) 831–843).

The urea derivatives of the general formula I therefore find an application for the prophylaxis and therapy of arterial vascular disorders such as acute myocardial infarct in combination with lysis therapy, post-infarct treatment, secondary prevention of myocardial infarct, reocclusion prophylaxis after lysis and dilatation, unstable angina pectoris, transitory ischaemic attacks, stroke, coronary bypass operation and reocclusion prophylaxis of the bypass, pulmonary embolism, peripheral arterial occlusive diseases, disseminating aneurysms, for the therapy of venous and microcirculatory vascular disorders such as deep vein thrombosis, disseminated intravascular clotting, post-operative and post-partum trauma, surgical or infectious shock, septicaemia, for the therapy in disorders with hyperreactive platelets, thrombotic thrombocytopenic purpura, preeclampsia, premenstrual syndrome, dialysis, extracorporal circulation; a further application is provided in inflammations and in the treatment of rumours. Osteoporosis can further be prevented by inhibition of osteoclast binding to the bone surface.

The compounds are tested in particular for their inhibitory effect on blood platelet aggregation and the adhesion of fibrinogen to blood platelets. Gel-filtered blood platelets from human donor blood are used, which are activated with ADP or thrombin.

The inhibition of the binding of fibrinogen to its receptor (glycoprotein IIb/IIIa) on intact, gel-filtered human platelets by the compounds according to the invention is tested. The $K_i$ value of the inhibition of binding of 125I-fibrinogen after stimulation with ADP (10 μM) is indicated. (Reference: J. S. Bennett and G. Vilaire, J. Clin. Invest. 64 (1979) 1393–1401; E. Kornecki et al., J. Biol. Chem. 256 (1981), 5695–5701; G. A. Marguerie et al., J. Biol. Chem. 254 (1979) 5357–5363; G. A. Marguerie et al., J. Biol. Chem. 255 (1980) 154–161.)

In this test, the following result was obtained for the compound of the following Example 1:

| Example | $K_i$ (μM), ADP-stimulated |
|---|---|
| 1 | 0.03 |

As a functional test, the inhibition of the aggregation of gel-filtered human platelets is measured after ADP or thrombin stimulation by the compounds according to the invention. The $IC_{50}$ value of the inhibition is indicated (reference: G. A. Marguerie et al., J. Biol. Chem. 254 (1979), 5357–5363).

In this test, the following results were obtained for the compounds of Examples 1, 6, 7, 8 and 10 below:

| Example | ADP-stimulated $IC_{50}$ (μM) | thrombin-stimulated $IC_{50}$ (μM) |
|---|---|---|
| 1 | 0.15 | 0.1 |
| 6 | 0.75 | 0.3 |
| 7 | 3.0 | 1.5 |
| 8 | 2.0 | 2.0 |
| 10 | 8.5 | 3.0 |

EXAMPLES

Example 1

(3-(4-(Aminoiminomethyl)phenyl)ureido)acetyl-L-aspartyl-L-phenylglycine a) Ethyl 3-(4-cyanophenyl)ureidoacetate A solution of 2.74 g (23 mmol) of 4-aminobenzonitrile in 10 ml of dimethoxyethane is added dropwise to a cooled solution (0° C.) of 3 g (23 mmol) of ethyl isocyanatoacetate in 10 ml of dimethoxyethane and the mixture is stirred at room temperature. The product is filtered off and washed with dimethoxyethane.

Yield: 2.56 g (45%) Melting point: 142° C.

b) Ethyl 3-(4-(ethoxyiminomethyl)phenyl)ureidoacetate hydrochloride

Dry HCl gas is introduced with stirring and cooling (0° C.) into a suspension of 2.3 g (9.3 mmol) of ethyl 3-(4-cyanophenyl)ureidoacetate in 50 ml of anhydrous ethanol. After 30 h, the mixture is concentrated in vacuo. The residue is stirred with ether and filtered off.

Yield: 2.68 g (87%) Melting point: 154°–157° C.

c) Ethyl 3-(4-aminoiminomethyl)phenyl)ureidoacetate hydrochloride 5.8 ml (1.5 equiv.) of ethanolic ammonia solution are added to a suspension of 2.68 g (8.1 mmol) of ethyl 3-(4-(ethoxyiminomethyl)phenyl)ureidoacetate hydrochloride in 25 ml of anhydrous ethanol. After stirring at room temperature for 5 days, the solid is filtered off and washed with ethanol.

Yield: 1.66 g (68%).

d) Ethyl 3-(4-(tert-butyloxycarbonylaminoiminomethyl) phenyl)ureidoacetate

A suspension of 1.71 g (5.7 mmol) of ethyl 3-(4-aminoiminomethyl)phenyl)ureidoacetate hydrochloride, 2.48 g (11.4 mmol) of di-tert-butyl dicarbonate and 2.86 g of sodium hydrogen carbonate in 100 ml of ethanol is heated at 50° C. for 10 h. The solid is filtered off and the filtrate is concentrated in vacuuo. The residue is treated with ethyl acetate and washed with water. After drying (Na2SO4), it is concentrated in vacuo.

Yield: 1.64 g (79%) Melting point: 167°–172° C.

e) Sodium 3-(4-(tert-butyloxycarbonylaminoiminomethyl) phenyl)ureidoacetate 1.6 g (4.4 mmol) of ethyl 3-(4-(tert-butyloxycarbonylaminoiminoemthyl)phenyl)ureidoacetate are treated with 0.18 g (4.4 mmol) of NaOH in 50 ml of ethanol and 1 ml of water. After stirring at room temperature for 20 h, the mixture is freeze-dried.

Yield: 1,52 g (97%) MS: 359 (M+1, Na salt), 337 (M+1, acid).

f) 3-(4-(tert-Butyloxycarbonylaminoiminomethyl)phenyl) ureidoacetyl-LAsp(OtBu)-L-phenylglycine-OtBu 0.5 g (1.4 mmol) of sodium 3-(4-(tert-butyloxycarbonylaminoiminomethyl)phenyl)ureidoacetate and 0.58 g (1.4 mmol) of L-aspartyl(OtBu)-L-phenylglycine-OtBu are dissolved in 30 ml of DMF and treated at 0° C. with stirring with 0.32 g (1.5 mmol) of dicyclohexylcarbodiimide, 0.19 g (1.4 mmol) of hydroxybenzotriazole and 2 ml of ethyl morpholine. After 72 h, solid is filtered off and the filtrate is concentrated in vacuo. The residue is taken up in ethyl acetate, the solution is washed with saturated sol hydrogen carbonate solu and water, and the organic phase is dried and concentrated in a rotary evaporator.

Yield: 1.02 g (100%).

g) (3-(4-(Aminoiminomethyl)phenyl)ureido)acetyl-L-aspartyl-L-phenylglycine 1.02 g (1.4 mmol) of 3-(4-(tert-butyloxycarbonylamino-iminomethyl)phenyl)ureidoacetyl-L-Asp(OtBu)-phenylglycine-OtBu are treated with 1.68 g (14.6 mmol) of trifluoroacetic acid (99%), 0.11 ml of water and 2 ml of dichloromethane and the mixture is left at room temperature for 24 h. It is concentrated in vacuo and chromatographed on Sephadex (LH-20) (butanol/glacial acetic acid/water).

Yield: 120 mg (15%) Melting point: 194° C. (dec.) $[\alpha]_D^{20}=$ +27.4° (c=0.365, glacial acetic acid)

$^1$H-NMR (D6-DMSO): δ=7.71 (d, 2H), 7.60 (d, 2H), 7.40–7.20 (m, 5H), 6.74 (m, 1H); 5.08 (m, 1H), 4.69 (m, 1H), 3.77 (m, 2H), 2.74–2.60 (m, 2H), 1.89 (s, 3H, acetic acid).

Example 2

(3-(4-(Amimoimiuomethyl)phenyl)ureido)acetyl-L-aspartyl (O-isopropyl)-L-phenylglycine isopropyl ester trifluoroacetate a) (3-(4-(tert-Butyloxycarbonylaminoiminomethyl)phenyl) ureido)acetyl-L-aspartyl(O-isopropyl)-L-phenylglycine isopropyl ester 1.39 g (3.87 mmol) of sodium (3-(4-(tert-butyloxycarbonylaminoiminomethyl)phenyl)ureido)acetate and 1.50 g (3.87 mmol) of L-aspartyl(O-isopropyl)-L-phenylglycine isopropyl ester are dissolved in 30 ml of DMF and treated at 0° C. with stirring with 0.88 g (4.26 mmol) of N,N'-dicyclohexylcarbodiimide, 0.52 g (3.87 mmol) of hydroxybenzotriazole and 0.40 ml of ethylmorpholine. After 18 h, the solid is filtered off and the filtrate is concentrated in vacuo. The residue is taken up in ethyl acetate and the solution is washed with saturated sodium hydrogen carbonate solution and water. After drying (MgSO4), hydrogen the organic phase is concentrated in vacuo. The residue (3.92 g) is reacted further without further purification.

b) (3-(4-(Aminoiminomethyl)phenyl)ureido)acetyl-L-aspartyl(O-isopropyl)-L-phenylglycine isopropyl ester trifluoroacetate 3.92 g (3.87 mmol) of (3-(4-(tert-butyloxycarbonylamino-iminomethyl)phenyl)ureido)acetyl-L-aspartyl(O-isopropyl)-L-phenylglycine isopropyl ester are treated with 3 ml of trifluoroacetic acid (99%) and 0.3 ml of water and the mixture is stirred at room temperature for 28 h. It is freeze-dried and the residue is chromatographed on silica gel (dichloromethane/methanol 9:1, then 8:2, then dichloromethane/methanol/glacial acetic acid 9:1:1).

Yield: 730 g (29%) Melting point: 104° C. to 109° C. MS (FAB): 570.2 [M+1]$^+$ [α]$_D$=+5(c=0.6, methanol)

$^1$H-NMR (D$_6$-DMSO): δ=9.20 (br.s, NH), 8.63 (d, NH), 8.31 (d, NH), 7.77 (d, 2H), 7.60 (d, 2H), 7.37 (m, 5H), 6.89 (t, NH), 5.31 (d, 1H), 4.86 (m, 3H), 3.76 (m, 2H), 2.74 (dd, 1H), 2.52 (dd, 1H), 1.26–1.03 (m, 12H).

Example 3

(3-(4-(Methoxycarbonylaminoiminomethyl)phenyl)ureido) acetyl-L-aspartyl(O-methyl)-L-phenylglycine methyl ester a) Ethyl (3-(4-(methoxycarbonylaminoiminomethyl)phenyl) ureido)acetate 1.74 g (22.7 mmol) of methyl chloroformate are added dropwise to a solution of 5 g (18.92 mmol) of ethyl (3-(4-(aminoiminomethyl)phenyl)ureido)acetate in 53 ml of triethylamine and 100 ml of DMF. After 7 d at room temperature, solid is filtered off and the filtrate is concentrated in vacuo. The residue is chromatographed on silica gel (ethyl acetate/methanol 95:5).

Yield: 5.18 g (85%).

b) Sodium (3-(4-(methoxycarbonylaminoiminomethyl) phenyl)ureido)acetate 5.15 g (15.98 mmol) of ethyl (3-(4-(methoxycarbonylaminoiminomethyl)phenyl)ureido)acetate are dissolved in 200 ml of ethanol and treated with 7.99 ml (15.98 mmol) of a 2N NaOH and the mixture is stirred at room temperature for 24 h. It is then concentrated in vacuo and the residue is freeze-dried.

Yield=4.90 g (97%).

c) (3-(4-(Methoxycarbonylaminoiminomethyl)phenyl) ureido)acetyl-L-aspartyl(O-methyl)-L-phenylglycine methyl ester 1.20 g (3.78 mmol) of sodium (3-(4-(methoxycarbonylaminoiminomethyl)phenyl)ureido)acetate and 1.98 g (3.78 mol) of L-aspartyl(O-methyl)-L-phenylglycine methyl ester trifluoroacetate are dissolved in 40 ml of DMF and treated at 0° C. with stirring with 0.86 g (4.16 mmol) of N,N'-dicyclohexylcarbodiimide, 0.51 g (3.78 mmol) of hydroxybenzotriazole and 1 ml of ethylmorpholine. After 20 h, solid is filtered off and the filtrate is concentrated in vacuo. The residue is taken up in ethyl acetate and the solution is washed with saturated sodium hydrogen carbonate solution and water. After drying (MgSO$_4$), the organic phase is concentrated in vacuo and the residue is chromatographed on silica gel (dichloromethane/ methanol 98:2, then 95:5).

Yield: 780 mg (36%) MS (FAB): 571.9 [M+1]$^+$ Melting point: 210° C. to 212° C. [α]$_D$=+49.73° (c=0.9, glacial acetic acid)

$^1$H-NMR (D$_6$-DMSO): δ=9.14 (br.s, NH), 8.37 (d, NH), 7.89 (d, 2H), 7.46 (d, 2H), 7.37 (m, 5H), 6.49 (t, NH), 5.40 (d, 1H), 4.83 (m, 1H), 3.77 (m, 2H), 3.60 (s, 3H), 3.57 (s, 3H), 2.77 (dd, 1H), 260 (dd, 1H).

Example 4

(3-(4-(Benzyloxycarbonylaminoiminomethyl)phenyl) ureido)acetyl-L-aspartyl(O-methyl)-L-phenylglycine methyl ester a) Ethyl (3-(4-(benzyloxycarbonylaminoiminomethyl) phenyl)ureido)acetate 0.50 g (1.66 mol) of ethyl (3-(4-(aminoiminomethyl) phenyl)ureido)acetate in 20 ml of THF is treated with 2.7 ml of 1N NaOH and cooled to 0° C. 0.29 ml (1.99 mmol) of benzyl chloroformate is added to this mixture and it is stirred at room temperature for 2 h. The pH is kept between 9 and 10 using 1N NaOH. The mixture is then treated with 50 ml of water and extracted with ethyl acetate. After drying (MgSO$_4$), the solvent is removed in vacuo and the residue is stirred with ether.

Yield: 0.4 g (60%).

b) Sodium (3-(4-(benzyloxycarbonylaminoiminomethyl) phenyl)ureido)acetate 0.74 g (1.86 mmol) of ethyl (3-(4-(benzyloxycarbonylaminoiminomethyl)phenyl)ureido) acetate in 100 ml of ethanol is treated with 1.86 ml of 1N NaOH and the mixture is stirred at room temperature for 6 h. The solvent is removed in vacuo and the residue is freeze-dried.

Yield: 0.73 g (99%).

c) 3-4-(Benzyloxycarbonylaminoiminomethyl)phenyl) ureido)acetyl-L-aspartyl(O-methyl)-L-phenylglycine methyl ester 0.73 g (1.86 mmol) of sodium (3-(4-(benzyloxycarbonylaminoiminomethyl)phenyl)ureido) acetate and 0.61 g (1.86 mmol) of L-aspartyl(O-methyl)-L-phenylglycine methyl ester trifluoroacetate are dissolved in 40 ml of DMF and treated at 0° C. with stirring with 0.42 g (2.04 mmol) of N,N'-dicyclohexylcarbodiimide and 0.25 g (1.86 mmol) of hydroxybenzotriazole. After 16 h, solid is filtered off and the filtrate is concentrated in vacuo. The residue is taken up in ethyl acetate and the solution is washed with saturated sodium hydrogen carbonate solution and water. After drying (MgSO$_4$), the organic phase is concentrated in vacuo and the residue is chromatographed on silica gel (dichloromethane/methanol 9:1).

Yield: 304 mg (25%) MS (FAB): 647.8 [M+1]$^+$ Melting point: 164° C. to 167° C. [α]$_D$=+38.71 (c=0.62; glacial acetic acid)

$^1$H-NMR (D$_6$-DMSO): δ=9.17 (s, NH), 9.00 (br.s, 2 NH), 8.79 (d, HN), 8.39 (d, NH), 7.93 (d, 2H), 7.50 (d, 2H), 7.39 (m, 10H), 6.53 (t, NH), 5.44 (d, 1H), 5.11 (s, 1H), 4.83 (m, 1H), 3.81 (d, 2H), 3.64 (s, 3H), 3.61 (s, 3H), 2.81 (dd, 1H), 2.64 (dd, 1H).

Example 5

(3-(4-(Aminoiminomethyl)phenyl)ureido)acetyl-L-aspartyl (O-methyl)-L-phenylglycine methyl ester trifluoroacetate a) (3-(4-(tert-Butyloxycarbonylaminoiminomethyl)phenyl) ureido)-acetyl-L-aspartyl(O-methyl)-L-phenylglycine methyl ester 1.92 g (5.34 mmol) of sodium (3-(4-(tert-butyloxycarbonylaminoiminomethyl)phenyl)ureido)acetate are dissolved in 30 ml of DMF and treated at 0° C. with stirring with 1.21 g (5.87 mmol) of N,N'-dicyclohexylcarbodiimide, 0.72 g (5.34 mmol) of hydroxybenzotriazole and 0.68 ml of ethyl morpholine. 2.18 g (5.34 mmol) of L-aspartyl(O-methyl)-L-phenylglycine methyl ester trifluoroacetate are then dissolved in 10 ml of DMF and added. After 24 h, solid is filtered off and the filtrate is concentrated in vacuo. The residue is taken up in ethyl acetate and the solution is washed with saturated sodium hydrogen carbonate solution and water. After drying (MgS04), the organic phase is concentrated in vacuo.

Yield: 2.10 g (64%).

b) (3-(4-(Aminoiminomethyl)phenyl)ureido)acetyl-L-aspartyl(O-methyl)-L-phenylglycine methyl ester trifluoroacetate 2.10 g (3.43 mmol) of (3-(4-(tert-butyloxycarbonylaminoiminomethyl)phenyl)ureido)acetyl- L-aspartyl(O-methyl)-L-phenylglycine methyl ester are treated with 3.95 g (34.3 mmol) of trifluoroacetic acid (99%) and 0.27 ml of water and the mixture is stirred at room temperature for 16 h. It is then concentrated in vacuo and the residue is chromatographed on silica gel (dichloromethane/ methanol/glacial acetic acid 9: 1:1).

Yield: 1.19 g (55%) MS (FAB): 513.8 [M+1]$^+$ Melting point: >140° C. $[\alpha]_D$=+9.48° (c=1.06, methanol)

$^1$H-NMR (D$_6$-DMSO): δ=9.50 (s, NH), 9.06 (br.s, 4 NH), 8.77 (d, NH), 8.37 (d, NH), 7.77 (d, 2H), 7.60 (d, 2H), 7.37 (m, 5H), 6.74 (t, NH), 5.43 (d, 1H), 4.80 (m, 1H), 3.79 (m, 2H), 3.63 (s, 3H), 3.60 (s, 3H), 2.80 (dd, 1H), 2.63 (dd, 1H).

Example 6

(3-(4-(Aminoiminomethyl)phenyl)ureido)acetyl-L-aspartyl (O-methyl)-L-phenylglycine methyl ester trifluoroacetate a) (3-(4-(tert Butyloxycarbonylaminoiminomethyl)phenyl) ureido)acetyl-L-aspartyl(O-tert-butyl)-L-phenylglycine methyl ester 1.00 g (2.78 mmol) of sodium (3-(4-(tert-butyloxycarbonylaminoiminomethyl)phenyl)ureido)acetate is dissolved in 30 ml of DMF and treated at 0° C. with stirring with 0.63 g (3.06 mmol) of N,N'-dicyclohexylcarbodiimide and 0.38 g (2.78 mmol) of hydroxybenzotriazole. 1.04 g (2.78 mmol) of L-aspartyl(O-tert-butyl)-L-phenylglycine methyl ester hydrochloride are then dissolved in 10 ml of DMF and added. After 18 h, solid is filtered off and the filtrate is concentrated in vacuo. The residue is taken up in ethyl acetate and the solution is washed with saturated sodium hydrogen carbonate solution and water. After drying (MgSO$_4$), the organic phase is concentrated in vacuo.

Yield: 2.01 g (100%, still contains N,N'-dicyclohexylurea).

b) (3-(4-(Aminoiminomethyl)phenyl)ureido)acetyl-L-aspartyl-L-phenylglycine methyl ester trifluoroaetate 2.01 g (2.78 mmol) of (3-(4-(tert-butyloxycarbonylamino-iminomethyl)phenyl)ureido)acetyl-L-aspartyl(O-tert-butyl)-L-phenylglycine methyl ester are dissolved in 2.16 ml of trifluoroacetic acid (99%) and 0.22 ml of water and the mixture is stirred at room temperature for 5 h. The solvent is removed in vacuo and the residue is chromatographed on Sephadex (LH-20) (butanol/water/glacial acetic acid).

Yield: 713 g (59%) MS (FAB): 499.8 [M+1] Melting point: >220° C. (dec.) $[\alpha]_D$=+19.35° (c=0.16, methanol)

$^1$H-NMR (D$_6$-DMSO): δ=9.09 (br.s, 2 NH), 8.89 (br.s, 2 NH), 8.69 (d, NH), 8.36 (d, NH), 7.74 (d, 2H), 7.57 (d, 2H), 7.37 (m, 5H), 6.66 (t, NH), 5.40 (d, 1H), 4.74 (m, 1H), 3.77 (m, 2H), 3.66 (s, 3H), 2.71 (dd, 1H), 2.53 (dd, 1H).

Example 7

3-((3-(4-(Aminoiminomethyl)phenyl)ureido)acetylamino)-3-phenyl-propionic acid a) Benzyl 3-((3-(4-(tert-butyloxycarbonylaminoiminomethyl)-phenyl)ureido) acetylamino-3-phenylpropionate 0.20 g (0.55 mmol) of sodium (3-(4)(tert-butyloxycarbonylaminoiminomethylphenyl)ureido)acetate is dissolved in 20 ml of DMF and treated at 0° C. with stirring with 0.12 g (0.60 mmol) of N,N'-dicyclohexylcarbodiimide and 0.07 g (0.55 mmol) of hydroxybenzotriazole. 0.14 g (0.55 mmol) of benzyl 3-amino-3-phenylpropionate is then dissolved in 5 ml of DMF and added. After 24 h, solid is filtered off and the filtrate is concentrated in vacuo. The residue is taken up in ethyl acetate and the solution is washed with saturated sodium hydrogen carbonate solution and water. After drying (MgSO$_4$), the organic phase is concentrated in vacuo. The residue (0.39 g) is reacted without further purification.

b) 3-((3-(4-(Aminoiminomethyl)phenyl)ureido) acetylamino)-3-phenylpropionic acid 0.38 g (0.66 mmol) of benzyl 3-((3-(4-(tert-butyloxycarbonylaminoiminomethyl)phenyl)ureido) acetylamino)-3-phenylpropionate is dissolved in 30 ml of DMF and treated with 0.07 g of Pd/C (10%). Hydrogen is then passed through for 24 h, solid is filtered off, the filtrate is concentrated in vacuo and the residue is treated with 1.53ml of trifluoroacetic acid (99%) and 0.15 ml of water. After stirring at room temperature for 48 h, the mixture is concentrated in vacuo and the residue is chromatographed on Sephadex (LH-20).

Yield: 28 g (11%) MS (FAB): 384.8 [M+1]$^+$ Melting point: >134° C. (dec.)

$^1$H-NMR (D$_6$-DMSO): δ=9.20–8.91 (br.s, 4NH), 8.60 (d, NH), 7.71 (d, 2NH), 7.57 (d, 2H), 7.31 (m, 5H), 6.63 (t, NH), 5.20 (m, 1H), 3.74 (m, 2H), 2.66 (m, 2H).

Example 8

(3-(4-(Aminoiminomethyl)phenyl)ureido)acetyl-L-aspartylbenzylamide a) (3-(4-(tert-Butyloxycarbonylaminoiminomethyl)phenyl) ureido)acetyl-L-aspartyl(O-tert-butyl)benzylamide 0.50 g (1.39 mmol) of sodium (3-(4-(tert-butyloxycarbonylaminoiminomethyl)phenyl)ureido)acetate is dissolved in 25 ml of DMF and treated at 0° C. with stirring with 0.32 g (1.53 mmol) of (N,N'-dicyclohexylcarbodiimide and 0.19 g (1.39 mmol) of hydroxybenzotriazole. 0.54 g (1.39 mmol) of L-aspartyl(O-tert-butyl)benzylamide hydrochloride is then dissolved in 5 ml of DMF and added. After 16 h, solid is filtered off and the filtrate is concentrated in vacuo. The residue is taken up in ethyl acetate and the solution is washed with saturated sodium hydrogen carbonate solution and water. After drying (MgSO$_4$), the organic phase is concentrated in vacuo.

Yield: 890 mg (100%, still contains N,N'-dicyclohexylurea).

b) (3-(4-(Aminoiminomethyl)phenyl)ureido)acetyl-L-aspartyl-benzylamide 0.89 g (1.39 mmol) of (3-(4-(tert-butyloxycarbonylamino-iminomethyl)phenyl)ureido)acetyl-L-aspartyl(O-tert-butyl)benzylamide is treated with 2.14 ml of trifluoroacetic acid (99%) and 0.32 ml of water and the mixture is stirred at room temperature for 22 h. It is then concentrated in vacuo and the residue is chromatographed on Sephadex (LH-20).

Yield: 440 mg (72%) MS (FAB): 441.6 [M+1]$^+$ Melting point: 209° C. to 211° C. (dec.) $[\alpha]_D$=−29.57° (c=0.58, DMF)

$^1$H-NMR (D$_6$-DMSO): δ=9.00 (m, 4NH), 8.40 (m, 2NH), 7.71 (d, 7.57 (d, 2H), 7.57 (d, 2H), 7.27 (m, 5H), 6.71 (t, NH), 4.29 (d, 2H), 3.80 (m, 2H), 2.70 (dd, 1H), 2.56 (dd, 1H).

Example 9 a) 3-(3-(3-(3-aminopropyl)ureido)benzoylamino)propionic acid a) Ethyl 3-(3-(3-tert-butyloxycarbonylaminopropyl)ureido) benzoate 2.00 g (8.12 mmol) of ethyl 3-isocyanatobenzoate (78%) are dissolved in 10 ml of DMF..A solution of 1.42 g (8.12 mmol) of 1-amino-3-tert-butyloxycarbonylaminopropane in 20 ml of DMF is slowly added dropwise at 2°–8°C. After stirring at room temperature for 2 h, the solvent is removed in vacuo, and the residue is treated with ethyl acetate and the mixture is washed with water. After drying (MgSO₄), solid is filtered off and the solvent is removed in vacuo. The residue is chromatographed on silica gel.
Yield: 2.55 g (86%).

b) 3-(3-(3-tert-Butyloxycarbonylaminopropyl)ureido) benzoic acid 2.50 g (6.84 mmol) of ethyl 3-(3-(3-tert-butyloxycarbonylaminopropyl)ureido)benzoate are dissolved in 80 ml of ethanol and treated with 3.42 ml of 2N NaOH. After 7 d at room temperature, the mixture is concentrated in vacuo. The residue is treated with water, and the mixture is acidified with citric acid and extracted with ethyl acetate. After drying (MgSO₄), solid is filtered off and the solvent is removed in vacuo.

c) Ethyl 3-(3-(3-(3-tert-butyloxycarbonylaminopropyl) ureido)benzoylamino)propionate 0.45 g (1.33 mmol) of 3-(3-(3-tert-butylcarbonylaminopropyl)ureido)benzoic acid is dissolved in 20 ml of DMF and treated at 0° C. with stirring with 0.30 g (1.47 mmol) of N,N'-dicyclohexylcarbodiimide and 0.18 g (1.33 mmol) of hydroxybenzotriazole. 0.21 g (1.33 mmol) of β-alanine ethyl ester hydrochloride and 0.51 ml of N-ethylmorpholine are then dissolved in 5 ml of DMF and added. After 20 h, solid is filtered off and the filtrate is concentrated in vacuo. The residue is taken up in ethyl acetate and the solution is washed with saturated sodium hydrogen carbonate solution and water. After drying (MgSO₄), the organic phase is concentrated in vacuo.
Yield: 0.65 g (100%, still contains N,N'-dicyclohexylurea).

d) 3-(3-(3-tert-Butyloxycarbonylaminopropyl)ureido) benzoylamino)propionic acid 0.61 g (1.33 mmol) of ethyl 3-(3-(3-(3-tert-butyloxycarbonylaminopropyl)ureido)benzoylamino)propionate is dissolved in 50 ml of ethanol and treated with 0.73 ml of 2N NaOH. After 25 h at room temperature, the solvent is removed in vacuo and the residue is treated with 20 ml of water and 20 ml of ethyl acetate and acidified with citric acid. The phases are separated and the aqueous phase is extracted a further two times with 20 ml of ethyl acetate each time. After drying (MgSO₄), the solvent is removed in vacuo and the residue (0.62 g) is employed without further purification.

e) 3-(3-(3-(3-Aminopropyl)ureido)benzoylamino)propionic acid 0.62 g (1.33 mmol) of 3-(3-(3-tert-butyloxycarbonylaminopropl)ureido)benzoylamino) propionic acid are treated with 2 ml of trifluoroacetic acid and 0.30 ml of water and the mixture is stirred at room temperature for 19 h. The solvent is removed in vacuo and the residue is chromatographed on Sephadex (butanol/water/ glacial acetic acid).
Yield: 380 mg (93%) MS (FAB): 309.8 [M+1]⁺ Melting point: Oil
¹H-NMR (D₆-DMSO, CF₃COOH): δ=7.83 (m, 1H), 7.57 (m, 1H), 7.33 (m, 2H), 3.46 (m, 2H), 3.19 (m, 2H), 2.83 (m, 2H), 1.71 (m, 2H).

Example 10

3-(3-(3-Aminopropyl)ureido)benzoyl-L-aspartyl-L-phenylglycine a) 3-(3-(3-tert-Butyloxycarbonylaminopropyl)ureido) benzoyl-L-aspartyl-L-phenylglycine tert-butyl ester 0.90 g (2.67 mmol) of 3-(3-(3-tert-butyloxycarbonylaminopropyl)ureido)benzoic acid is dissolved in 15 ml of DMF and treated at 0° C. with stirring with 0.61 g (2.93 mmol) of N,N'-di-cyclohexylcarbodiimide and 0.36 g (2.67 mmol) of hydroxybenzotriazole. 1.11 g (2.67 mmol) of L-aspartyl(O-tert-butyl)-L-phenylglycine tert-butyl ester hydrochloride and 0.34 ml of N-ethylmorpholine are then dissolved in 5 ml of DMF and added. After 17 h, solid is filtered off and the filtrate is concentrated in vacuo. The residue is taken up in ethyl acetate and the solution is washed with saturated sodium hydrogen carbonate solution and water. After drying (MgSO₄), the organic phase is concentrated in vacuo.
Yield: 1.82 g (98%).

b) 3-(3-(3-Aminopropyl)ureido)benzoyl-L-aspartyl-L-phenylglycine 1.82 g (2.61 mmol) of 3-(3-(3-tert-butyloxycarbonylamino-propyl)ureido)benzoyl-L-aspartyl (O-tert-butyl)-L-phenylglycine tert-butyl ester are treated with 4 ml of trifluoroacetic acid (99%) and 0.4 ml of water and the mixture is stirred at room temperature for 17 h. The solvent is removed in vacuo and the residue is chromatographed on Sephadex (butanol/water/glacial acetic acid).
Yield: 1.04 g (82%) MS (FAB): 487.2 [M+1]⁺ Melting point: >58° C. [α]$_D$ =+27.12 (c=1.18, methanol)
¹H-NMR (D₆-DMSO): δ=9.83 (s, OH), 9.61 (d, NH), 8.86 (d, NH), 7.86 (s, OH), 7.71 (br.s, 3 NH), 7.60 (d, NH), 7.34 (m, 9H), 6.46 (t, NH), 5.29 (d, 1H), 4.86 (m, 1H), 3.17 (m, 2H), 2.80 (m, 4H), 1.71 (m, 2H).

Example 11

3-(4-(Aminoiminomethyl)benzyl)-3-benzyloxyureido) acetyl-L-aspartyl-L-phenylglycine a) 4-(Benzyloxyiminomethyl)benzonitrile 3.07 g (23.4 mmol) of 4-cyanobenzaldehyde are dissolved in 150 ml of ethanol, treated with 3.74 g (23.4 mmol) of o-benzylhydroxyamine hydrochloride and 11.7 ml of 2N NaOH and the mixture is heated to reflux for 4 h. The solvent is removed in vacuo, and the residue is treated with water and extracted with ethyl acetate. After drying (MgSO₄), the organic extract is concentrated and the residue is recrystallized from ethanol.
Yield: 3.48 g (63%) Melting point: 95° C.

b) 4-(Benzylaminomethyl)benzonitrile 3.44 g (15 mmol) of 4-(benzyloximinomethyl) benzonitrile in 120 ml of ethanol are cooled to −15° C. 4.46 g (48 mmol, 4.85 ml) of borane-pyridine complex are then added dropwise in the course of 10 minutes and then 26 ml of ethanolic HCl solution in the course of 20 minutes. After stirring at room temperature for 24 h, the resulting solid is filtered off, dissolved in dichloromethane and the solution is washed with water and sodium hydrogen carbonate solution. The organic phase is dried and concentrated in vacuo.
Yield: 2.73 g (76%).

c) Ethyl (3-(4-cyanobenzyl)-3-benzyloxyureido)acetate 2.73 g (11 mmol) of 4-(benzyloxyaminomethyl) benzonitrile are dissolved in 75 ml of DMF and added dropwise at 0° C. to a solution of 1.48 g of ethyl isocyanatoacetate in 75 ml of DMF. The mixture is heated at 50° C. for 3 d, then concentrated in vacuo. The residue is taken up in ethyl acetate and the solution is washed with water. The organic phase is dried (MgSO₄) and concentrated in vacuo. The residue is dissolved in a little ethyl acetate and precipitated with ether/petroleum ether. The precipitate produced is reacted without further purification.
Yield: 2.99 g Melting point: 82°–84° C.

d) Ethyl (3-(4-(ethoxyiminomethyl)benzyl)-3-benzyloxyureido)acetate 2.99 g (8.14 mmol) of ethyl (3-(4-cyanobenzyl)-3-benzyloxyureido)acetate are dissolved in 250 ml of ethanol and cooled to −30° C. Dry HCl gas is introduced into the solution. After 24 h, excess HCl gas is driven out by nitrogen and the solvent is removed in vacuo. The residue crystallizes from ethyl acetate/ether.

Yield: 2.83 g (84%) Melting point: 120°–122° C.

e) Ethyl (3-(4-(aminoiminomethyl)benzyl)-3-benzyloxyureido)acetate 2.83 g (6.84 mmol) of ethyl (3-(4-(ethoxyiminomethyl) benzyl)-3-benzyloxyureido)acetate are dissolved in 100 ml of ethanol and treated with 6.74 ml (6.84 mmol) of ethanolic ammonia solution. After 24 h at room temperature, the solvent is removed in vacuo and the residue is recrystallized from ethyl acetate/ether.

Yield: 2.34 g (89%) Melting point: 205°–208° C.

f) Ethyl (3-(4-(tert-butyloxycarbonylaminoiminomethyl) benzyl)-3-benzyloxyureido)acetate 2.30 g (5.98 mmol) of ethyl (3-(4-(aminoiminomethyl) benzyl)-3-benzyloxyureido)acetate in 200 ml of ethanol are treated with 2.61 g (11.96 mmol) of di-tert-butyl dicarbonate and 1.50 g (17.94 mmol) of sodium hydrogen carbonate. After 2 d at 50° C., solid is filtered off and the filtrate is concentrated in vacuo.

Yield: 2.79 g (96%) Melting point: 86°–90° C.

g) Sodium (3-(4-(tert-butyloxycarbonylaminoiminomethyl) benzyl)-3-benzyloxyureido)acetate 2.78 g (5.74 mmol) of ethyl (3-(4-(tert-butyloxycarbonylaminoiminomethyl)benzyl)-3-benzyloxyureido)acetate in 50 ml of ethanol are treated with 0.23 g (5.74 mmol) of NaOH and 1.2 ml of water and the mixture is stirred at room temperature for 18 h. The solvent is removed in vacuo and the residue is freeze-dried.

Yield: 2.6 g (94%) Melting point: 129°–137° C.

h) (3-(4-tert-Butyloxycarbonylaminoiminomethyl)-3-benzyloxyureido)acetyl-L-aspartyl(O-tert-butyl)-L-phenylglycine tert-butyl ester 0.5 g (1.04 mmol) of sodium (3-(4-(tert-butyloxycarbonyl-aminoiminomethyl)benzyl)-3-benzyloxyureido)acetate is dissolved in 20 ml of DMF and treated at 0° C. with stirring with 0.24 g (1.15 mmol) of N,N'-dicyclohexylcarbodiimide and 0.14 g (1.04 mmol) of hydroxybenzotriazole. 0.43 g (1.04 mmol) of L-aspartyl(O-tert-butyl)-L-phenylglycine tert-butyl ester hydrochloride is then added. After 19 h, solid is filtered off and the filtrate is concentrated in vacuo. The residue is taken up in ethyl acetate and the solution is washed with saturated sodium hydrogen carbonate solution and water. After drying (MgSO$_4$), the organic phase is concentrated in vacuo and the product is reacted without further purification.

Yield: 0.93 g (still contains dicyclohexylurea).

i) (3-(4-(Aminoiminomethyl)benzyl)-3-benzyloxyureido) acetyl-L-aspartyl-L-phenylglycine 0.93 g (1.04 mmol) of (3-(4-(tert-butyloxycarbonylaminoiminomethyl)benzyl)-3-benzyloxyureido)acetyl-L-aspartyl(O-tert-butyl)-L-phenylglycine tert-butyl ester is treated with I ml of trifluoroacetic acid (99%) and 0.1 ml of water and the mixture is stirred at room temperature for 24 h. The solvent is removed in vacuo and the residue is chromatographed on Sephadex (butanol/water/glacial acetic acid).

Yield: 0.184 g (29%) MS: 605 [M+1]$^+$ Melting point: 203°–210° C.

$^1$H-NMR (D$_6$-DMSO): δ=9.80 (s, 2NH), 9.40 2NH), 8.40 (d, NH), 8.10 (d, NH), 7.74 (d, 2H), 7.49 (d, 2H), 7.43–7.00 (m, 10H), 4.86 (m, 4H), 4.67 (m, 1H), 4.54 (d, 1H), 3.89 (dd, 1H), 3.63 (dd, 1H), 2.69 (dd, 1H), 2.46 (dd, 1H).

The following can be obtained analogously:

Example 12

(3-(4-(Aminoiminomethyl)benzyl)ureido)acetyl-L-aspartyl-L-phenylglycine

Example 13

(3-(4-(Aminoiminomethyl)phenyl)thioureido)acetyl-L-aspartyl-L-phenylglycine

Example 14

(3-(4-(Aminoiminomethyl)benzyl)-3-hydroxyureido)acetyl-L-aspartyl-L-phenylalanine

Example 15

3-(3-(2-Guanidinoethyl)ureido)benzoyl-L-aspartyl-L-valine

Example 16

1-(4-(Aminoiminomethyl)phenylcarbamoyl)pyrrolidin-2-yl-carbonyl-L-aspartyl-L-phenylglycine

Example 17

4-(3-(2-Amino-2-iminoethyl)ureido)benzoyl-L-aspartyl-L-phenylglycine

Example 18

(3-(4-Guanidinophenyl)ureido)acetyl-L-aspartyl-L-phenylglycine

Example 19

2-(3-(4-(Aminoiminomethyl)phenyl)ureido)propionyl-L-aspartyl-L-phenylglycine

Example 20

3-(3-(4-(Aminoiminomethyl)phenyl)ureido)propionyl-L-aspartyl-L-phenylglycine

Example 21

((3-(4-(Aminoiminomethyl)phenyl)ureido)acetyl-L-aspartylamino-phenylmethylsulphonyl)urea

Example 22

(3-(4-(Aminoiminomethyl)phenyl)-3-methylureido)acetyl-L-aspartyl-L-phenylglycine

Example 23

(3-(4-(Aminoiminomethyl)phenyl)-1,3-dimethylureido) acetyl-L-aspartyl-L-phenylglycine.

Example 24

(3-(4-(Guanidinophenyl)ureido)acetyl-L-aspartyl-L-phenylglycine

Example 25

3-(3-(4-(Aminoiminomethyl)phenyl)ureido)acetylamino)-3-(oxazol-2-yl)propionic acid

Example 26

3-(3-(4-(Aminoiminomethyl)phenyl)ureido)acetylamino) pent-4-ynoic acid

Example 27

(3-(4-(Aminoiminomethyl)phenyl)-3-benzylureido)acetyl-L-aspartyl-L-phenylglycine

Example 28

(3-(4-(((1-Acetoxyethoxy)carbonyl)aminoiminomethyl) phenyl)ureido)acetyl-L-aspartyl(O-methyl)-L-phenylglycine methyl ester

Example A

Emulsions containing 3 mg of active compound per 5 ml can be prepared according to the following recipe:

| Active compound | 0.06 g |
|---|---|
| Neutral oil | q.s. |
| Sodium carboxymethylcellulose | 0.6 g |
| Polyoxyethylene stearate | q.s. |
| Pure glycerol | 0.6 to 2 g |
| Aromatizers | q.s. |
| Water (demineralized or distilled) | to 100 ml |

Example B

Tablets can be prepared according to the following formulation:

| Active compound | 2 mg |
|---|---|
| Lactose | 60 mg |
| Maize starch | 30 mg |
| Soluble starch | 4 mg |
| Magnesium stearate | 4 mg |
| | 100 mg |

Example C

The following composition is suitable for the preparation of soft gelatine capsules containing 5 mg of active compound per capsule:

| Active compound | 5 mg |
|---|---|
| Mixture of triglycerides from coconut oil | 150 mg |
| Capsule contents | 155 mg |

Example D

The following formulation is suitable for the preparation of sugar coated tablets:

| Active compound | 3 mg |
|---|---|
| Maize starch | 100 mg |
| Lactose | 55 mg |
| Sec-calcium phosphate | 30 mg |
| Soluble starch | 3 mg |
| Magnesium stearate | 5 mg |
| Colloidal silicic acid | 4 mg |
| | 200 mg |

Example E

Sugar-coated tablets, containing an active compound according to the invention and another therapeutically active substance:

| Active compound | 6 mg |
|---|---|
| Propanolol | 40 mg |
| Lactose | 90 mg |
| Maize starch | 90 mg |
| Sec-calcium phosphate | 34 mg |
| Soluble starch | 3 mg |
| Magnesium stearate | 3 mg |
| Colloidal silicic acid | 4 mg |
| | 270 mg |

Example F

Sugar-coated tablets, containing an active compound according to the invention and another therapeutically active substance:

| Active compound | 5 mg |
|---|---|
| Pirlindol | 5 mg |
| Lactose | 60 mg |
| Maize starch | 90 mg |
| Sec-calcium phosphate | 30 mg |
| Soluble starch | 3 mg |
| Magnesium stearate | 3 mg |
| Colloidal silicic acids | 4 mg |
| | 200 mg |

Example G

Capsules, containing an active compound according to the invention and another therapeutically active substance:

| Active compound | 5 mg |
|---|---|
| Nicergoline | 5 mg |
| Maize starch | 185 mg |
| | 195 mg |

Example H

Injection solutions containing 1 mg of active compound per ml can be prepared according to the following recipe:

| Active compound | 1.0 mg |
|---|---|
| Polyethylene glycol 400 | 0.3 mg |
| Sodium chloride | 2.7 mg |
| Water for injection to | 1 ml |

We claim:
1. Urea derivatives of the formula I

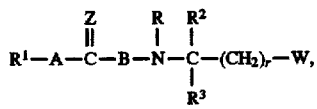

in which r denotes an integer from 0 to 1;

Z denotes oxygen or sulphur;

W denotes —$COW^1$ or tetrazolyl;

$W^1$ denotes hydroxyl, $(C_1-C_4)$-alkoxy, benzyloxy, amino or mono- or di-$((C_1-C_8)$-alkyl)amino;

A denotes

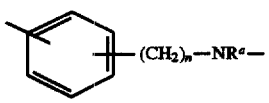

in which n stands for an integer from 0 to 1;

B denotes —NR$^b$—(CH$_2$)$_m$—CO—, in which m stands for an integer from 1 to 2; R$^a$ and R$^b$ independently of one another denote hydrogen, hydroxyl, (C$_1$–C$_{18}$)-alkyl, (C$_6$–C$_{14}$)-aryl, (C$_6$–C$_{14}$)-aryl-(C$_1$–C$_8$)-alkyl, (C$_1$–C$_{28}$)-alkoxy, (C$_6$–C$_{14}$)-aryloxy, or (C$_6$–C$_{14}$)-aryl-(C$_1$–C$_8$)-alkoxy;

R denotes hydrogen or (C$_1$–C$_6$)-alkyl;

R$^1$ denotes —NHX or —C(=NX)—NH$_2$;

X denotes hydrogen, (C$_1$–C$_6$)-alkylcarbonyl, (C$_1$–C$_6$)-alkoxycarbonyl, (C$_1$–C$_{18}$)-alkylcarbonyloxy(C$_1$–C$_6$)-alkoxycarbonyl, (C$_6$–C$_{14}$)-aryl-(C$_1$–C$_6$)-alkoxycarbonyl, hydroxyl, or a radical of the formula II

R'—NH—C(=N—R")—     (II)

where R' and R" independently of one another stand for hydrogen, (C$_1$–C$_6$)-alkoxycarbonyl, (C$_1$–C$_6$)-alkylcarbonyl, (C$_1$–C$_{18}$)-alkylcarbonyloxy-(C$_1$–C$_6$)-alkoxycarbonyl, (C$_6$–C$_{14}$)-aryl-(C$_1$–C$_6$)-alkoxycarbonyl or hydroxyl;

R$^2$ denotes hydrogen or phenyl;

R$^3$ denotes —CO—NH—R$^4$, where —NH—R$^4$ stands for the radical of an α-amino acid, its ω-amino-(C$_2$–C$_8$)-alkylamide or its (C$_1$–C$_8$)-alkyl or benzyl ester, or where R$_4$ denotes methyl which is substituted by an amino acid side chain and also by a radical from the series —SO$_2$—OH, —SO$_2$— NHR$^9$ and tetrazolyl;

R$^9$ denotes hydrogen, aminocarbonyl, (C$_1$–C$_{18}$)-alkylaminocarbonyl, (C$_3$–C$_8$)-cycloalkylaminocarbonyl, (C$_1$–C$_{18}$)-alkyl or (C$_3$–C$_8$)-cycloalkyl;

and their physiologically tolerable salts.

2. Urea derivatives according to claim 1, wherein, in the formula I, r denotes the number 1;

W denotes —COW$^1$;

W$^1$ denotes hydroxyl, (C$_1$–C$_4$)-alkoxy, or benzyloxy;

A denotes

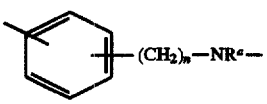

in which n stands for the numbers 0 or 1;

B denotes —NR$^b$—(CH$_2$)$_m$—CO— in which m stands for the numbers 1 or 2;

R denotes hydrogen,

X denotes hydrogen, (C$_1$–C$_6$)-alkoxycarbonyl, (C$_1$–C$_6$)-alkylcarbonyl, (C$_1$–C$_{18}$)-alkylcarbonyloxy-(C$_1$–C$_6$)-alkoxycarbonyl, (C$_6$–C$_{14}$)-aryl-(C$_1$–C$_6$)-alkoxycarbonyl or a radical of the formula

R'—NH—C=N—R", in which R' and R" independently of one another stand for hydrogen, (C$_1$–C$_6$)-alkylcarbonyl, (C$_1$–C$_6$)-alkoxycarbonyl, (C$_1$–C$_{18}$)-alkylcarbonyloxy-(C$_{1-C6}$)-alkoxycarbonyl or (C$_6$–C$_{14}$)-aryl-(C$_1$–C$_6$)-alkoxycarbonyl;

R$^2$ denotes hydrogen;

R$^3$ denotes —CO—NH—R$^4$, where —NH—R$^4$ stands for the radical of an α-amino acid, its ω-amino-(C$_2$–C$_8$)-alkylamide or its (C$_1$–C$_8$)-alkyl or benzyl ester, or where R$_4$ denotes methyl which is substituted by an amino acid side chain and also by a radical from the series —SO$_2$—OH, —SO$_2$— NHR$^9$ and tetrazolyl.

3. Urea derivatives according to claim 2 in which W' denotes methoxy, ethoxy, 2-propyloxy, isobutyloxy or tert-butyloxy.

4. Urea derivates according to claim 2, in which R$^3$ denotes —CO—NH—R$^4$, where —NH—R$^4$ stands for the radical of the α-amino acids valine, lysine, phenylalanine, phenylglycine or 4-chlorophenylglycine, their ω-amino-(C$_2$–C$_8$)-alkylamides or their (C$_1$–C$_8$)-alkyl or benzyl esters.

5. Urea derivatives according to claim 4, wherein the (C$_1$–C$_8$)-alkyl ester of the α-amino acids is the methyl, ethyl, isopropyl, isobutyl or tert-butyl ester.

6. Process for the preparation of compounds of the general formula I according to claim 1, comprising a fragment condensation of a compound of the general formula III

with a compound of the general formula IV

where the radicals A, B, W, Z, R, R$^1$, R$^2$ and R$^3$ and also r are defined as indicated in claim 1.

7. Pharmaceutical preparation, containing one or more compounds of the general formula I according to claim 1 and/or one or more physiologically tolerable salts thereof as active compound together with pharmaceutically acceptable excipients and additives.

8. Process for the production of a pharmaceutical preparation, containing one or more compounds of the general formula I according to claim 1, and/or one or more physiologically tolerable salts thereof, comprising mixing such compounds into a suitable administration form together with pharmaceutically acceptable excipients and additives.

9. Method for inhibiting platelet aggregation, the metastasis of carcinoma cells and osteoclast binding to a bone surface, which comprises administering to a host in need thereof an effective dose of a urea derivative or physiologically tolerable salt thereof according to claim 1.

* * * * *